United States Patent
McGonigle et al.

(10) Patent No.: US 9,993,441 B2
(45) Date of Patent: Jun. 12, 2018

(54) CONTROLLED RELEASE MATRIX BARRIER STRUCTURE FOR SUBCUTANEOUS MEDICAL DEVICES

(71) Applicant: SurModics, Inc., Eden Prairie, MN (US)

(72) Inventors: Joseph Schmidt McGonigle, Minneapolis, MN (US); Aleksey V. Kurdyumov, Maplewood, MN (US); Jeffrey J. Missling, Eden Prairie, MN (US); Nathan A. Lockwood, Minneapolis, MN (US); Kevin W. Burton, Hoover, AL (US); Beth A. Petersen, Glencoe, MN (US)

(73) Assignee: Surmodics, Inc., Eden Prairie, MN (US)

(*) Notice: Subject to any disclaimer, the term of this patent is extended or adjusted under 35 U.S.C. 154(b) by 190 days.

(21) Appl. No.: 14/669,571

(22) Filed: Mar. 26, 2015

(65) Prior Publication Data

US 2015/0196497 A1 Jul. 16, 2015

Related U.S. Application Data

(63) Continuation-in-part of application No. 12/980,468, filed on Dec. 29, 2010, now abandoned.

(60) Provisional application No. 61/291,071, filed on Dec. 30, 2009.

(51) Int. Cl.
| | |
|---|---|
| *A61F 2/00* | (2006.01) |
| *A61K 9/70* | (2006.01) |
| *A61K 31/573* | (2006.01) |
| *A61K 9/00* | (2006.01) |
| *A61K 47/34* | (2017.01) |
| *A61L 29/06* | (2006.01) |
| *A61L 29/14* | (2006.01) |
| *A61L 29/16* | (2006.01) |
| *A61L 31/04* | (2006.01) |
| *A61F 2/07* | (2013.01) |
| *A61F 2/82* | (2013.01) |
| *A61L 31/10* | (2006.01) |

(52) U.S. Cl.
CPC .......... *A61K 9/7007* (2013.01); *A61K 9/0024* (2013.01); *A61K 31/573* (2013.01); *A61K 47/34* (2013.01); *A61L 29/06* (2013.01); *A61L 29/14* (2013.01); *A61L 29/16* (2013.01); *A61F 2/07* (2013.01); *A61F 2/82* (2013.01); *A61L 31/04* (2013.01); *A61L 31/10* (2013.01); *A61L 2300/404* (2013.01); *A61L 2300/406* (2013.01)

(58) Field of Classification Search
None
See application file for complete search history.

(56) References Cited

U.S. PATENT DOCUMENTS

| | | | |
|---|---|---|---|
| 4,595,713 A | 6/1986 | St John | |
| 4,874,612 A | 10/1989 | Deasy | |
| 5,215,532 A | 6/1993 | Atkinson | |
| 5,700,286 A | 12/1997 | Tartaglia et al. | |
| 5,702,717 A | 12/1997 | Cha et al. | |
| 5,707,647 A | 1/1998 | Dunn et al. | |
| 5,876,452 A | 3/1999 | Athanasiou et al. | |
| 6,126,919 A | 10/2000 | Stefely et al. | |
| 6,165,486 A | 12/2000 | Marra et al. | |
| 6,331,311 B1 | 12/2001 | Brodbeck et al. | |
| 6,344,035 B1 | 2/2002 | Chudzik et al. | |
| 6,406,745 B1 | 6/2002 | Talton | |
| 6,475,235 B1 | 11/2002 | Jayaraman | |
| 6,477,428 B1 | 11/2002 | Skinner et al. | |
| 6,503,556 B2 | 1/2003 | Harish et al. | |
| 6,673,767 B1 | 1/2004 | Brodbeck et al. | |
| 6,742,522 B1 | 6/2004 | Baker et al. | |
| 6,887,270 B2 | 5/2005 | Miller et al. | |
| 6,890,583 B2 | 5/2005 | Chudzik et al. | |
| 6,936,052 B2 | 8/2005 | Gellman et al. | |
| 7,008,667 B2 | 3/2006 | Chudzik et al. | |
| 7,368,126 B2 | 5/2008 | Chen et al. | |

(Continued)

FOREIGN PATENT DOCUMENTS

| | | |
|---|---|---|
| EP | 1917971 | 5/2008 |
| EP | 2611868 | 7/2013 |

(Continued)

OTHER PUBLICATIONS

Beletsi, A et al., "Effect of Preparative Variables on the Properties of poly(dl-lactide-co-glycolide)—methoxypoly (ethyleneglycol) Copolymers Related to Their Application in Controlled Drug Delivery," International Journal of Pharmaceuticals, 182 (1999) pp. 187-197.

(Continued)

*Primary Examiner* — James W Rogers
(74) *Attorney, Agent, or Firm* — Pauly, DeVries Smith & Deffner LLC (57) ABSTRACT

A biocompatible polymeric controlled release matrix barrier structure for delivery of one or more bioactive agents from an implantable medical device is described. In an embodiment, a biocompatible polymeric controlled release matrix barrier structure is included. The biocompatible polymeric controlled release matrix can include a body structure formed of a compliant material comprising one or more compliant biocompatible polymers and one or more bioactive agents. The body structure can define a central aperture through which a subcutaneous element of an implantable medical device passes. Other embodiments are included herein.

14 Claims, 4 Drawing Sheets

(56) References Cited

U.S. PATENT DOCUMENTS

| | | |
|---|---|---|
| 7,396,538 B2 | 7/2008 | Granada et al. |
| 7,544,673 B2 | 6/2009 | Dewitt et al. |
| 8,920,921 B2 | 12/2014 | Bowman et al. |
| 2002/0150622 A1 | 10/2002 | Philbrook et al. |
| 2003/0026967 A1 | 2/2003 | Joseph et al. |
| 2003/0105245 A1 | 6/2003 | Amsden |
| 2003/0114637 A1 | 6/2003 | Gogolewski |
| 2004/0039441 A1 | 2/2004 | Rowland et al. |
| 2004/0052859 A1 | 3/2004 | Wu et al. |
| 2004/0116025 A1 | 6/2004 | Gogins et al. |
| 2004/0224132 A1 | 11/2004 | Roe et al. |
| 2004/0249437 A1 | 12/2004 | Sundar |
| 2005/0021131 A1 | 1/2005 | Venkatraman et al. |
| 2005/0079202 A1 | 4/2005 | Chen et al. |
| 2005/0271701 A1 | 12/2005 | Cottone, Jr. et al. |
| 2007/0280988 A1 | 12/2007 | Ludwig et al. |
| 2008/0009781 A1 | 1/2008 | Anwar et al. |
| 2008/0015676 A1 | 1/2008 | Kantor |
| 2008/0118541 A1 | 5/2008 | Pacetti |
| 2008/0118727 A1 | 5/2008 | Andersen |
| 2009/0076350 A1 | 3/2009 | Bly et al. |
| 2009/0124535 A1 | 5/2009 | Markland et al. |
| 2009/0292367 A1 | 11/2009 | Borden |
| 2009/0306120 A1 | 12/2009 | Lim et al. |
| 2010/0158978 A1 | 6/2010 | Markland |
| 2010/0168807 A1 | 7/2010 | Burton et al. |
| 2010/0209476 A1* | 8/2010 | Lim ................... A61L 31/10 424/426 |
| 2011/0159072 A1 | 6/2011 | Missling et al. |
| 2011/0251450 A1* | 10/2011 | Pagani ............... A61B 17/3478 600/16 |
| 2012/0077028 A1 | 3/2012 | Bowman et al. |
| 2012/0078155 A1 | 3/2012 | Bowman et al. |

FOREIGN PATENT DOCUMENTS

| | | | |
|---|---|---|---|
| JP | 2001335623 | 12/2001 | |
| JP | 2005519654 | 7/2005 | |
| JP | 2011503183 | 1/2011 | |
| JP | 2012513473 | 7/2012 | |
| JP | 2013543521 | 12/2013 | |
| WO | 1997038676 | 10/1997 | |
| WO | WO 2007088402 A2 * | 8/2007 | ......... A61L 24/0094 |
| WO | 2007118139 | 10/2007 | |
| WO | 2009064442 | 5/2009 | |
| WO | 2010075298 | 7/2010 | |
| WO | 2012030821 A1 | 3/2012 | |
| WO | 2012030823 A1 | 3/2012 | |
| WO | 2016154541 | 9/2016 | |

OTHER PUBLICATIONS

Brannon-Peppas, Lisa "Polymers in Controlled Drug Delivery," Medical Plastics and Biomaterials Magazine / MPB Article Index MPB archive, Nov. 97 1997, pp. 1-11.
"Communication Pursuant to Rules 161(1) and 162 EPC," for European Patent Application No. 11757461.6, dated Apr. 8, 2013 (2 pages).
"Final Office Action," for U.S. Appl. No. 12/644,097, dated Feb. 28, 2013 (28 pages.).
"Final Office Action," for U.S. Appl. No. 12/980,468, dated Feb. 25, 2013 (16 pages).
"Final Office Action," for U.S. Appl. No. 12/643,580, dated Mar. 23, 2015 (24 pages).
"Final Office Action," for U.S. Appl. No. 12/644,097, dated Apr. 9, 2014 (20 pages).
"Final Office Action," for U.S. Appl. No. 12/644,097, dated Jun. 11, 2015 (18 pages).
"Final Office Action," for U.S. Appl. No. 13/221,464, dated Dec. 4, 2014 (47 pages).
"Final Office Action," dated April 9,2012 in co-pending U.S. Appl. No. 12/644,097, "Bioactive Terpolymer Compositions and Methods of Making and Using Same," (16 pages).
"Final Office Action," dated Sep. 27, 2012 in U.S. Appl. No. 12/643,580, "Bioactive Spray Coating Compositions and Methods of Making and Uses Thereof," (8 pages).
"International Preliminary Report on Patentability," from PCT Application No. PCT/US2011/049730, dated Mar. 14, 2013, 8 pages.
"International Preliminary Report on Patentability," from PCT Application No. PCT/US2011/049735, dated Mar. 14, 2013, 10 pages.
"International Search Report and Written Opinion," from International Application No. PCT/US2011/049730, dated Nov. 18, 2011, pp. 1-20.
"International Search Report and Written Opinion," from International Application No. PCT/US2011/049735, dated Nov. 18, 2011, pp. 1-15.
Lu, Chengfei et al., "Synthesis and Aggregation Behavior of four types of different Shaped PCL-PEG Block Copolymers," Polymer International, vol. 55, 2006, pp. 694-700.
"Methoxy Polyethylene Glycols Technical Data Sheet," INEOS http://www.ineos.com/Show-Document/?Grade-Methoxy %20Polyethylene%20Glycol%20350&BU-INEOS%20Oxide &DocumentType-Technical%20Datac%20Sheet, 2004 (4 pages).
Mundargi, Raghavendra C. et al., "Development and Evaluation of Novel Biodegradable Microspheres Based on poly(D,L-Lactide-co-glycolide) and poly(e-caprolactone) for Controlled Delivery of Doxycycline in the Treatment of Human Periodontal Pocket: In Vitro and In Vivo Studies," Journal of Controlled Release, vol. 119, 2007, pp. 59-68.
"Non-Final Office Action," For U.S. Appl. No. 12/980,468, dated Jan. 26, 2015 (17 pages).
"Non-Final Office Action," dated Mar. 16, 2012 in co-pending U.S. Appl. No. 12/643,580, "Bioactive Spray Coating Compositions and Methods of Making and Uses Thereof," (31 Pages).
"Non-Final Office Action," dated Oct. 11, 2011 in co-pending U.S. Appl. No. 12/644,097, "Bioactive Terpolymer Compositions and Methods of Making and Using Same" (48 pages).
"Non-Final Office Action," for Japanese Patent Application No. 2013-527191, dated May 26, 2015 (14 pages) with English Translation.
"Non-Final Office Action," for U.S. Appl. No. 12/643,580, dated May 20, 2014 (10 pages).
"Non-Final Office Action," for U.S. Appl. No. 13/221,464, dated May 9, 2014 (33 pages).
"Non-Final Office Action," for U.S. Appl. No. 12/644,097, dated Jul. 19, 2013 (37 pages).
"Non-Final Office Action," for U.S. Appl. No. 12/643,580 dated Sep. 9, 2015 (13 pages).
"Non-Final Office Action," for U.S. Appl. No. 12/644,097, dated Sep. 11, 2014 (26 pages).
"Non-Final Office Action," for U.S. Appl. No. 13/221,415, dated Feb. 6, 2014 (16 pages).
"Non-Final Office Action," for U.S. Appl. No. 13/221,464, dated Jul. 17, 2015 (41 pages).
"Non-Final Office Action," dated Oct. 12, 2012 in U.S. Appl. No. 12/980,468, "Controlled Release Matrix," (19 pages).
"Non-Final Office Action," dated Sep. 20, 2012 in U.S. Appl. No. 12/644,097, "Bioactive Terpolymer Compositions and Methods of Making and Using Same," (38 pages).
"Notice of Allowance," for U.S. Appl. No. 13/221,415, dated Aug. 1, 2014 (20 pages).
"Response Final Office Action," for U.S. Appl. No. 12/980,468, dated Feb. 25, 2013 and filed with the USPTO May 22, 2013 (9 pages).
"Response Non-Final Office Action," for U.S. Appl. No. 12/644,097, dated Sep. 11, 2014 and filed with the USPTO Feb. 11, 2015 (10 pages).
"Response to Communication Pursuant to Rules 161(1) and 162 EPC," for European Patent Application No. 11757461.6, dated Apr. 8, 2013 and filed with the EPO Aug. 6, 2013 (9 pages).
"Response to Final Office Action," for U.S. Appl. No. 12/643,580, dated Mar. 23, 2015 and filed with the USPTO Jul. 22, 2015 (8 pages).

(56) References Cited

OTHER PUBLICATIONS

"Response to Final Office Action," for U.S. Appl. No. 13/221,464, dated Dec. 4, 2014 and filed with the USPTO Mar. 4, 2015 (16 pages).

"Response to Final Office Action," dated Apr. 9, 2014 in co-pending U.S. Appl. No. 12/644,097, filed with the USPTO Jul. 9, 2014 (10 pages).

"Response to Final Office Action," dated Dec. 27, 2012 in U.S. Appl. No. 12/643,580, "Bioactive Spray Coating Compositions and Methods of Making and Uses Thereof," 5 pages.

"Response to Final Office Action," dated February 28, 2013, in co-pending U.S. Appl. No. 12/644,097, filed with USPTO May 24, 2013, (12 pages).

"Response to Final Office Action," dated Jul. 9, 2012 in U.S. Appl. No. 12/644,097, "Bioactive Terpolymer Compositions and Methods of Making an Dusing Same," (10 pages).

"Response to Non Final Office Action," dated Jan. 3, 2012 in U.S. Appl. No. 12/644,097, "Bioactive Terpolymer Compositions and Methods of Making and Using Same," (8 pages).

"Response to Non-Final Office Action," for U.S. Appl. No. 12/643,580, dated May 20, 2014 and filed with the USPTO Nov. 20, 2014 (7 pages).

"Response to Non-Final Office Action," for U.S. Appl. No. 12/644,097, dated Jul. 19, 2013 and filed with the USPTO Dec. 19, 2013 (7 pages).

"Response to Non-Final Office Action," for U.S. Appl. No. 12/980,468, dated Oct. 12, 2012 and filed with the USPTO Jan. 11, 2013 (9 pages).

"Response to Non-Final Office Action," for U.S. Appl. No. 13/221,464, dated May 9, 2014 and filed with the USPTO Sep. 9, 2014 (18 pages).

"Response to Non-Final Office Action," for U.S. Appl. No. 13/221,415, dated Feb. 6, 2014 and filed with the USPTO May 6, 2014 (13 pages).

"Response to Non-Final Office Action," dated Jun. 14, 2012 in co-pending U.S. Appl. No. 12/643,580 6 pages.

"Response to Non-Final Office Action," dated Sep. 20, 2012, in co-pending U.S. Appl. No. 12/644,097, filed with USPTO Jan. 18, 2013, (10 pages).

Sawhney, "Rapidly degraded terpolymers of dl-lactide, glycolide, and [epsilon]—caprolactone with increased hydrophilicity by copolymerization with ployethers," Journal of Biomedical Materials Research, Wiley, New York, NY, US vol. 24, No. 10, Oct. 1, 1990, pp. 1397-1411.

Srisa-Ard, Mangkorn et al., "Synthesis and characterization of a random terpolymer of L-lactide, e-caprolactone and glycolide," Society of Chemical Industry, Polymer International, vol. 50, Issue 8 (Jul. 20, 2001) pp. 891-896.

"Viscous," Merriam-Webster Dictionary (http:www.merriam-webster.com/dictionary/viscous) 2015 (4 pages).

"International Search Report and Written Opinion," for PCT Application No. PCT/US2016/024228 dated Jun. 29, 2016 (11 pages).

\* cited by examiner

CONTROLLED RELEASE MATRIX BARRIER STRUCTURE FOR SUBCUTANEOUS MEDICAL DEVICES

This application is a continuation-in-part application of prior U.S. application Ser. No. 12/980,468, filed Dec. 29, 2010, which claims the benefit of U.S. Provisional Application No. 61/291,071, filed Dec. 30, 2009, the content of all of which is herein incorporated by reference.

BACKGROUND

Many surgical interventions require the placement of a medical device into the body. While necessary and beneficial for treating a variety of medical conditions, the placement of metal or polymeric devices in the body can result in complications. Some of these complications include: increased risk of infection; initiation of a foreign body response resulting in inflammation and fibrous encapsulation; and initiation of a wound healing response and hyperplasia. These and other complications must be dealt with when introducing a metal or polymeric device into the body.

SUMMARY

A biocompatible polymeric controlled release matrix barrier structure for use with implantable medical devices having subcutaneous elements is described. In various embodiments, the polymeric controlled release matrix barrier structure comprises a compliant film comprising one or more compliant biocompatible polymers and one or more bioactive agents. In another embodiment, the biocompatible polymeric controlled release matrix barrier structure comprises an elastomeric collar comprising one or more elastomeric biocompatible polymers and one or more bioactive agents. In various embodiments, the elastomeric collar comprises at least one elastomeric co-polymer comprising elastomeric and non-elastomeric subunits. In another embodiment, the elastomeric collar comprises a blend of at least one elastomeric polymer and at least one non-elastomeric polymer. In various embodiments, the biocompatible polymer is biostable. In another embodiment, the biocompatible polymer is biodegradable. In a more particular embodiment, the controlled release matrix barrier structure comprises a polymer selected from the group consisting of: polycaprolactone (PCL), poly(lactic acid), poly(lactic-co-glycolic acid), and poly(ethylene-co-vinyl acetate). In various embodiments, one or more polymers are cross-linked. In another embodiment, the polymers are not cross-linked. The bioactive agent can be selected from the group consisting of: antibiotics, antiseptics, antiviral agents, enzyme inhibitors, anti-pyretics, immunomodulators, analgesics, local anesthetics, and cell response modifiers.

A method for applying a controlled release matrix barrier structure to a surface of an implantable medical device is also described. In various embodiments, the method comprises applying a compliant biocompatible polymeric controlled release matrix barrier structure to the implantable medical device under tension, wherein the controlled release matrix barrier structure comprises a compliant film that is capable of conforming to the surface of the implantable medical device and one or more bioactive agents. In various embodiments, the compliant film conforms to and adheres to the surface of the implantable medical device without an adhesive. In another embodiment, an adhesive is applied to the implantable medical device or the polymeric film to increase adhesion of the compliant film to the device. In various embodiments, the film has a length and the length of film applied to the implantable medical device can be altered to modify a dosage of bioactive agent. In another embodiment, the film has a width between about 5 mm and about 10 mm; and a thickness between about 50 µm and about 250 µm.

Also described is a method for applying a controlled release matrix barrier structure to a surface of an implantable medical device, wherein the controlled release matrix barrier structure comprises an elastomeric biocompatible polymeric controlled release matrix barrier structure comprising an elastomeric collar and one or more bioactive agents. In various embodiments, the step of applying the controlled release matrix barrier structure comprises elastic deformation of the collar by application of a stress on the collar; placement of the collar around the implantable medical device; and release of the stress on the collar, wherein the collar substantially returns to its initial shape upon release of the stress.

Also described are methods of making a biocompatible elastomeric controlled release controlled release matrix barrier structure, comprising a procedure selected from the group consisting of: melt extrusion, injection molding, spray casting, and spray coating.

BRIEF DESCRIPTION OF THE DRAWINGS

Aspects may be more completely understood in connection with the following drawings, in which.

While embodiments are susceptible to various modifications and alternative forms, specifics thereof have been shown by way of example and drawings, and will be described in detail. It should be understood, however, that the scope herein is not limited to the particular embodiments described. On the contrary, the intention is to cover modifications, equivalents, and alternatives falling within the spirit and scope herein.

DETAILED DESCRIPTION

As described above, the placement of devices in the body can result in an increased risk of infection. This is especially true in the context of devices that include subcutaneous elements (device elements that reside partially in the body and partially out of the body passing through the skin). The term "tunneled" is sometimes used to describe devices with subcutaneous elements such as tunneled catheters. Tunneled catheters are passed under the skin from an insertion site to a separate exit site, where the catheter and its attachments emerge from underneath the skin. Tunneled catheters, such as those used for chronic hemodialysis access, as well as other catheters with subcutaneous elements, are prone to infection that can develop into a systemic infection known as catheter-related blood stream infection (CRBSI). One of the primary routes to infection is contamination from the catheter entry site. Bacteria from the external environment or patient's skin can migrate down the catheter until they reach the blood contacting the distal portion of the catheter.

The invention described herein provides a novel controlled release matrix barrier structure for use with implantable medical devices having subcutaneous elements. These barrier structures can prevent infections that would otherwise start from contamination at the site where the physical barrier provided by the skin is compromised, such as where a catheter pass through the skin. As used herein, the term "subcutaneous" specifically includes transdermal and transcutaneous applications, unless the context dictates otherwise. As such, embodiments herein specifically include those where the skin barrier is physically compromised by having a physical element pass through the skin barrier. In various embodiments, the controlled release matrix barrier structure is a biocompatible film that can be used for the delivery of one or more bioactive agents from an implantable medical device. As used herein, the term "film" is used here to refer to a flexible material that is conformable to the surface of an implantable medical device. As used herein, the term "conformable" means that the material is malleable and can deform to follow the contours of the surface of the underlying medical device. In various embodiments, the flexible film is able to adhere to the surface of an implantable medical device without the use of an adhesive. In another embodiment, the conformable film readily adheres to itself, particularly when applied under tension. The term "film" can be used interchangeably with the words "wrap" and "tape." In another embodiment, the controlled release matrix barrier structure is configured as an elastomeric "collar" or "sheath" that can be applied to the surface of an implantable medical device. As used herein, the term "collar" or "sheath" refers to a controlled release matrix barrier structure that can be deformed when a stress is applied to fit over the surface of an implantable medical device, wherein upon release of the stress, the collar relaxes substantially to back to its original configuration. As used herein, the term "substantially" means that the collar returns to its original configuration to a great extent or degree, although, in some instance, the collar may not relax completely back to its original configuration (for example, where the underlying medical device imparts a stress on the collar that prevents it from returning to its original configuration, or where the force applied to the collar exceeds the elastic limit of the device). In contrast to the conformable film, the collar can be attached to the underlying medical device by being clipped or snapped around the device (elastic deformation), rather than being applied under tension such that it stretches and conforms (plastic deformation) to the surface of the underlying device.

One unique feature of the controlled release matrix described herein, is that it can be applied to an implantable medical device by a physician or other medical practitioner after manufacturing of the underlying medical device is complete, for example, while in the operating room. This enables the implantable medical device to be manufactured separately from the controlled release matrix barrier structure, thus alleviating concerns with the presence of bioactive agent in the manufacturing facility. For example, when a medical device is manufactured with a bioactive agent, the bioactive agent must be segregated to prevent contamination of other products. Additionally, engineering controls must be in place to protect workers from the bioactive agent and an analytical chemistry laboratory is needed to test the product and to test the cleanliness of services. In addition to simplifying the manufacturing process, the controlled release matrix barrier structure configuration described herein allows the implantable medical device and the controlled release matrix barrier structure to be packaged separately. As such, the controlled release matrix barrier structure can be stored in a suitable environment (e.g., under refrigeration, for example at a temperature between about 4° C. and about 8° C.), and the implantable medical device can be stored at room temperature. As such, valuable refrigerator space is not consumed unnecessarily storing the medical device. Furthermore, the post-manufacturing application of the controlled release matrix barrier structure provides the medical practitioner with increased flexibility in the selection of bioactive agent. For example, the controlled release matrix barrier structure can be manufactured using a variety of different bioactive agents, such that the medical practitioner can select the matrix with the desired bioactive agent for a given patient or therapy. For example, the controlled release matrix barrier structure can be packaged within a sterile single use packaging, including, but not limited to sealed foil, or TYVEK™ pouches. The single use package can be provided in different size (in the case of the collar configuration) or lengths (in the case of the film configuration), for example, single use packages of the conformable film can be provided in lengths of at least about 5 mm and up to about 100 mm. And finally, the dosage of bioactive agent can be increased by increasing the amount of the controlled release matrix that is applied to the device. Although the dosage and/or concentration of bioactive agent within the controlled release matrix can vary, for example, depending upon the particular bioactive agent in use, it is envisioned that the controlled release matrix would include a concentration of bioactive agent of at least about 2% by weight, and up to about 50% by weight, or a dosage between about 20 micrograms to about 500 micrograms per $mm^3$, or a dosage between about 21 micrograms and about 525 micrograms per millimeter of length (assuming a film about 5 mm to about 10 mm wide and about 100 microns to about 200 microns thick, or about 7 millimeters wide and about 150 microns thick).

As used herein, the term "biocompatible" refers to a substance that has substantially no known toxic or adverse effects on a biological system. In various embodiments, the controlled release matrix is biodegradable. As used herein, the term "biodegradable" refers to a substance that can be partially or fully chemically degraded, for example, via hydrolysis, or decomposed by biological processes, for example, by enzymatic activity, such that the polymer chains are converted into biologically acceptable, and progressively smaller, compounds. In various embodiments, the biodegradable substance includes one or more hydrolytically, chemically, biochemically, and/or proteolytically labile groups, including, but not limited to an ester moiety, amide moiety, anhydride moiety, specific peptide sequences, and generic peptide sequences. One advantage of using a degradable matrix is that the material degrades within the patient as a result of natural biological processes, reducing concerns associated with long-term effects of implanted biostable polymers. In various embodiments, the controlled release matrix is configured to degrade within about 1 month to about 12 months, or in less than about 6 months after implantation in vivo.

In an alternate embodiment, the controlled release matrix is biostable (i.e., non-degradable within the body). In yet another embodiment, the controlled release matrix is configured to be removable by the medical practitioner, after the bioactive agent is deemed to be no longer necessary. For example, it may be desirable to remove the controlled release matrix barrier structure and/or underlying medical device in situations where the implantable device is used to stabilize a bone or joint during healing, such as orthopedic hardware used to repair fractured bones, or a temporarily placed catheter or for hardware, such as external fixation pins that span the patient's skin.

Controlled Release Matrix Barrier Structure

As described above, the controlled release matrix barrier structure described herein can be applied to a medical device by a medical practitioner in the operating room, after manufacture of the implantable medical device is complete. In various embodiments, the controlled release matrix barrier structure is applied as a conformable film. In another embodiment, the controlled release matrix barrier structure is applied as an elastomeric collar or sheath.

Film

Figure 1:
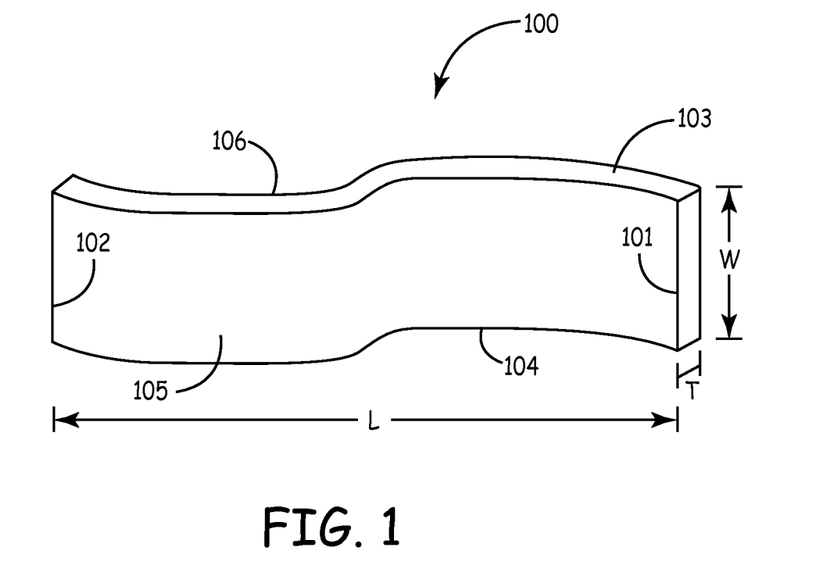
FIG. 1 is a schematic illustration of a controlled release matrix barrier structure.

In various embodiments, the controlled release matrix barrier structure is a flexible polymeric film 100, as shown in FIG. 1 that has a length "L" that extends between a first 101 and a second 102 end; a width "W" that extends between a first 103 and a second 104 edge; and a thickness "T" that extends between a first 105 and a second 106 side. The term "film" can be used interchangeably with the words "wrap" and "tape." As used herein, the term "film" is used here to refer to a flexible material that is conformable to an underlying surface. In various embodiments, the film is able to conform to the surface of a medical device to which it is applied. As used herein, the term "conform" refers to the plastic deformation of the film that results when the film is applied to the surface of the medical device under tension, such that the film is slightly taut or stretched as it is being wound around the device. Applying the film under tension will not only increase the conformance of the film to the surface of the medical device, but it will increase the tenacity by which the flexible film adheres to itself. The amount of tension can vary, but, in general the force required to generate the tension is well within the physical abilities of a medical practitioner. In various embodiments, the film is applied under a tension of at least about 50 grams and up to about 500 grams.

In various embodiments, the controlled release matrix barrier structure comprises a compliant polymeric material. As used herein, the term "compliant" refers to a polymeric material or polymer that can stretch when subjected to force, conform to the surface geometry of the underlying substrate over which it is stretched, and not break, crack, or fissure as a result of the stretching and conforming actions. The compliant material may undergo plastic deformation in order to conform to the underlying surface geometry. As used herein, the term "plastic deformation" refers to an irreversible change in the internal molecular structure (or microstructure) of the controlled release matrix barrier structure due to the applied force. However, it is noted that it is possible that the stress does not cause a permanent change, for example if the applied stress is less than the internal forces of the material, such that the internal forces are able to oppose the applied force, allowing the object to assume a new equilibrium state and return to its original shape when the force is removed (elastic deformation). In particular, a compliant material suitable for use herein should elongate and permanently deform but not break when it stretched/wrapped around the implantable medical device.

The mechanical properties that can be used to define a compliant material include tensile strength, % elongation to break, yield stress and Young's Modulus, for example. The term "tensile strength" refers to the stress required to break a sample and is expressed in Pascals (Pa). In general, a suitable compliant material has a tensile strength of at least about 1 MPa, or between about 1 MPa and about 100 MPa. The phrase "% elongation to break" refers to the elongation of a sample when it breaks. It is usually expressed as a percent. In general, compliant materials have an elongation-to-break, of at least about 100%, or at least about 200%. Yield stress refers to the work (per unit volume) required to produce yield (deformation) in the polymer (units are in $J/cm^3$) and is determined by the maximum point in the stress/strain curve for a material that is followed by a yielding deformation. It is noted that yield can depend upon the rate at which the load is applied to the polymer. Young's Modulus is the ratio of stress to strain. It is also called the modulus of elasticity or the tensile modulus. Young's Modulus for a given fiber or material can change with the amount of strain. Whereas rigid materials tend to have a high Young's modulus, compliant materials have lower values.

Figure 3:
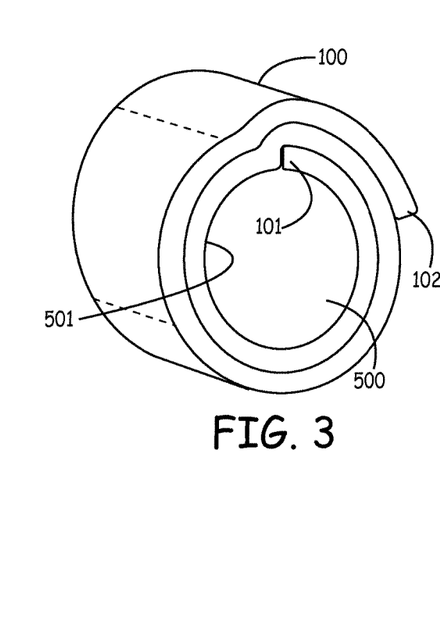
FIG. 3 is a schematic illustration of a controlled release matrix barrier structure applied to a medical device with multiple film layers.
Figure 4:
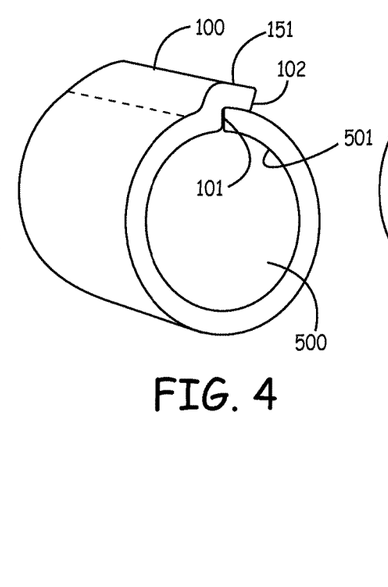
FIG. 4 is a schematic illustration of a controlled release matrix barrier structure applied to a medical device as a single layer film.

In various embodiments (shown in FIG. 2), one or more loops 150 of film 100 are wrapped around a surface 501 of an underlying medical device 500 to form essentially a single layer. It should be understood that the term "single layer" is meant to allow for overlap 151 between the loops 150 of film 100. Additionally, as shown more specifically in FIG. 4, the term "single layer" can also include overlap 152 between the first 101 and second 102 ends of the film 150. In another embodiment, shown in FIG. 3, the film 100 can be wrapped around the underlying medical device 500 more than once, to form multiple layers of film 100. In general, as the length L of film 100 applied to the medical device 500 increases, the amount of bioactive agent available for release increases. As such, the dosage of bioactive agent released can be modified by altering the length L or amount of film 100 applied to the medical device 500.

Figure 2:
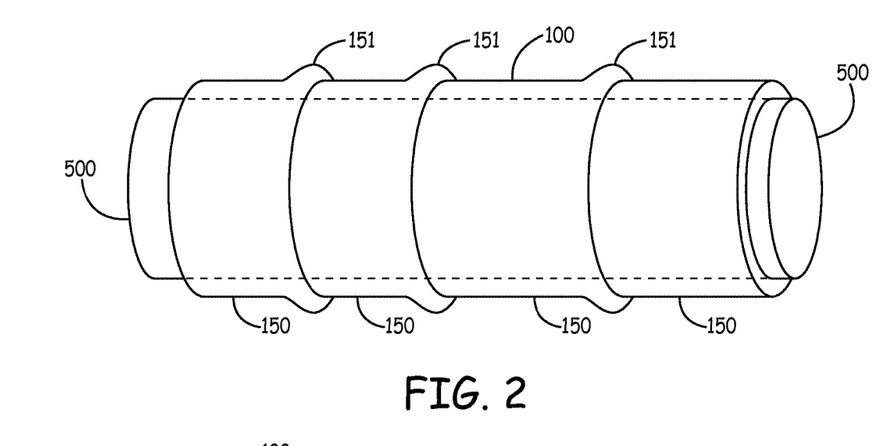
FIG. 2 is a schematic illustration of a controlled release matrix barrier structure applied to a medical device as a single layer film.

The width W and thickness T of controlled release matrix barrier structure can vary. In particular, a particular width W and/or thickness T may be better suited for one type of implantable medical device whereas a different width W and/or thickness T may be better suited for another type of implantable medical device. In general, the controlled release matrix barrier structure has a width of at least about 1 mm and up to about 25 mm, or between about 5 mm and about 10 mm. The thickness of the controlled release matrix barrier structure is generally at least about 25 µm and up to about 500 µm, or between about 50 µm and 250 µm thick. The length L of controlled release matrix barrier structure applied to a device can be selected by the medical practitioner. In various embodiments, the length L is selected to be sufficient to wrap around a medical device at least once. In an alternate embodiment, the length L is selected to wrap around a medical device multiple times. In various embodiments, the multiple loops 150 of the controlled release matrix barrier structure 100 overlap along the length of the device 500 (as shown in FIG. 2). In another embodiment, the multiple loops 150 of the controlled release matrix barrier structure 100 form multiple layers on the surface of the device 500 (shown in FIG. 3)

The ability of the matrix to conform to the surface of the underlying medical device and to self-adhere reduces the likelihood that the matrix will migrate after it is applied. Thus, in various embodiments, the film is applied to the device without the use of an adhesive. Although not necessary, a biocompatible adhesive can be applied to increase the bond between the film and the surface of the underlying medical device. A variety of biocompatible adhesives are known, and include, but are not limited to natural and synthetic adhesives. Examples of biocompatible adhesives include, but are not limited to, synthetic urethane based polymers or protein based adhesives. In some embodiments, the biocompatible adhesive can include a terpolymer or blend of terpolymers having adhesive properties. Such terpolymer adhesives are described in greater detail below.

Collar

In an alternate embodiment, the controlled release matrix barrier structure is configured as a collar 100' (or sheath) that is placed on or around the implantable medical device 500 by a medical practitioner. Whereas as the flexible film (described above) undergoes a plastic deformation to conform to the surface of the underlying device when applied under tension, a collar is manufactured using an elastomeric material that has a pre-existing shape or configuration that is substantially corresponds to the surface or a portion of the surface of the underlying medical device. To apply the collar to the device, the collar is deformed (elastic deformation) by the application of a stress or force on the collar and positioned around at least a portion of the implantable medical device. After the collar is positioned, the stress is released and the collar substantially returns to its initial shape such that the collar attaches to the underlying medical device by a "snap-fit" or "stretch-fit" mechanism. The term "stress" or "force" can refer to one or more of the following forces: tensile (pulling) force, compressive (pushing) force, shear, bending, or torsion (twisting) force. It is noted that, as deformation occurs, the internal forces of the collar material oppose the applied force. If the applied stress is not too large these opposing forces may completely resist the applied force, allowing the object to assume a new equilibrium state and to return to its original shape when the force is removed. This is what is known as elastic deformation (or elasticity). Elastic deformation can be described by Hooke's Law for restoring forces, where the stress is linearly proportional to the strain. It is likewise noted that forces in excess of the elastic limit of a material may cause a permanent (irreversible) deformation of the object. This is what is known as plastic deformation or plasticity. It is also noted that the surface of the implantable medical device may apply a force to the collar when the collar is in position, such that, once applied to the implantable medical device, the collar is not able to fully return to its original configuration.

As with compliant materials, the mechanical properties that can be used to define a compliant material include tensile strength, % elongation to break, yield stress and Young's Modulus. As used herein, the term "elastomer" or "elastomeric" refers to a polymer or material that can be stretched easily to high extensions (e.g., 3 to 10 times the original dimension) and which rapidly recovers to its original dimension. Typically, elastomers are materials having a tensile strength of at least about 10 MPa, or between about 20 MPa and about 200 MPa and a high elongation-to-break, generally at least about 300% and up to about 1000%. Methods for determining mechanical properties of a polymer are known, and include, for example, ASTM D882-09 Standard Test Method for Tensile Properties of Thin Plastic Sheeting and ASTM D1790-99 Standard Tst Method for Brittleness Temperature of Plastic Sheeting by Impact.

Figure 5:
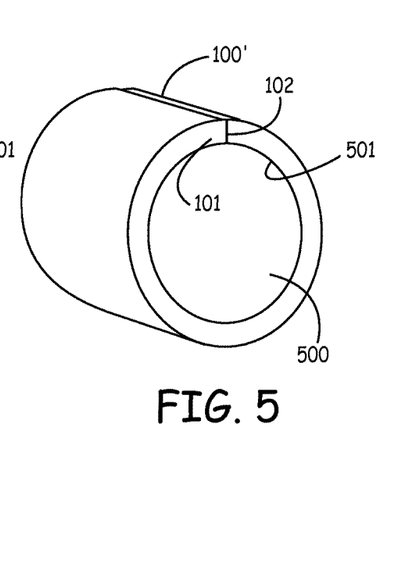
FIG. 5 is a schematic illustration of a controlled release matrix barrier structure applied to a medical device as a collar.

In various embodiments, the "collar" configuration of the controlled release matrix barrier structure is applied as a single layer without any overlap (See, FIG. 5), although in other embodiments, it may be desirable for the collar to overlap. If desired, the thickness of the "collar" can vary, such that a collar having a particular thickness can be selected by the medical practitioner to provide a desired dosage. The precise configuration of the collar would depend upon the medical device to which it would be applied. In general, the collar is configured to encircle and/or follow the contours of the underlying medical device. In an alternate embodiment, the collar includes one or more fastening mechanisms 200 that are configured to mate with one or more receptacles 520 on the underlying medical device 500 to secure the collar thereto.

Polymeric Matrix

As used herein, the term "controlled release matrix" refers to a polymeric matrix that is capable of delivering a bioactive agent at a controlled rate for a period of time. In various embodiments, controlled release matrix barrier structures herein include a controlled release matrix. Although there may be an initial burst phase, the overall release kinetics of the bioactive agent from the matrix are generally linear, such that a relatively constant supply of bioactive agent is released over the desired time period. The time period may vary from several hours to several months, depending upon the bioactive agent and its intended use. In general, it is preferable that the percentage of bioactive agent released from the controlled matrix over the treatment period be relatively high (e.g., at least about 50%, at least about 75%, at least about 90%, or at least about 95%) to avoid waste of unreleased bioactive agent.

There are many mechanisms by which a bioactive agent can be released from a controlled release matrix. Two mechanisms include diffusion and/or degradation. Diffusion occurs when the bioactive agent is released either through pores in the polymer matrix or by passing between polymer chains of the matrix. In a diffusion system, the bioactive agent can be dispersed throughout the matrix, or localized within a reservoir adjacent to or within the matrix. In a reservoir system, a reservoir of bioactive agent, for example, solid drug, dilute solution, or highly concentrated drug solution within a polymer matrix is surrounded by a controlled release material through which the bioactive agent is able to diffuse. In a degradable system, the bioactive agent is released as the matrix is degraded in vivo. Bioactive agent can also be released by a combination of the two mechanisms. In various embodiments of the controlled release matrix barrier structure described herein, the release of the bioactive agent is driven by a combination of both diffusion and degradation. The release rate can be controlled by varying the drug to polymer ratio (e.g., a higher drug concentration tends to result in a faster rate of release), by varying the chemistry of polymeric matrix (e.g., inclusion of polymers having a Tg of less than about 40° C. or less than about 0° C. would tend to result in a faster elution rate than polymers with Tgs greater than 40° C., polymers that absorb water tend to elute drug more quickly than more hydrophobic polymers that do not absorb water. These variables can be controlled by the selection of materials used in the manufacturing process.

In various embodiments, the controlled release matrix barrier structure is configured to release at least about 40% and up to about 60%, or at least 50% of the bioactive agent within 7 days of implantation. In another embodiment, the controlled release matrix barrier structure is configured to release at least about 80% or up to about 100%, or at least 90% of the bioactive agent within 21 days after implantation.

In various embodiments, the controlled release matrix is biodegradable. In a more particular embodiment, the controlled release matrix includes a biodegradable polyester. Examples of biodegradable polyesters include, but are not limited to: polycaprolactone (PCL), polylactic acid (PLA), polyglycolide (PGA), and copolymers thereof, such as poly(lactic-co-glycolic acid) polymers (PLGA) and poly(glycolide-co-carolactone) (PGC). Polycaprolactone (PCL) refers to a biodegradable polyester prepared by ring opening polymerization of ε-caprolactone using a catalyst such as stannous octanoate. Polycaprolactone has a melting point of about 60° C. and is degraded by hydrolysis of its ester linkages under physiological conditions.

Polylactic acid (PLA) is a biodegradable, thermoplastic polyester that can be produced by bacterial fermentation of renewable resources such as corn, starch or sugarcane and has a melting temperature between about 173° C. and about 178° C.

Polyglycolide (PGA) is a biodegradable, thermoplastic polyester prepared from glycolic acid by polycondensation or ring-opening polymerization. It has a melting point of between about 225° C. to about 230° C.

Poly(lactic-co-glycolic acid) polymers (PLGA) refers to a biodegradable copolymer of lactic and glycolic acid formed by random ring-opening co-polymerization of monomers of glycolic acid and lactic acid. During polymerization, the monomeric units are linked together by ester linkages, thus yielding an aliphatic polyester. PLGAs are amorphous and have a glass transition temperature between about 40° C. and 60° C. In general, the PLGA copolymer has a weight average molecular weight between about 1000 Da to about 50,000 Da, or between about 5000 Da and 25,000 Da. The ratio of lactic acid to glycolic acid can vary. In general and increase in the amount of lactic acid results in a polymer that degrades more slowly. An increase in glycolic acid results in a polymer that degrades more quickly. Additionally, an increase in glycolic acid tends to decrease the glass transition temperature (Tg) and water penetration into the polymer, which can result in a faster release of compounds. In general, the ratio of lactic acid to glycolic acid is between about 100:0 to about 25:75, or between about 60:40 and 40:60, or about 50:50.

In some embodiments, the matrix can include terpolymers or blends of terpolymers having adhesive properties. By way of example, in some embodiments, the matrix can include a blend of (a) a first poly(D,L-lactide-co-glycol lactide-co-ε-caprolactone) having a molecular weight ($M_w$) of from 75,000 to 250,000 Daltons and a polydispersity index (PDI) of less than 2.0, and (b) a second poly(D,L-lactide-co-glycolide-co-ε-caprolactone) having a molecular weight ($M_w$) of 130,000 Daltons or less and a polydispersity index (PDI) of less than 2.0; the second poly(D,L-lactide-co-glycolide-co-ε-caprolactone) having a molecular weight ($M_w$) that is less than the first poly(D,L-lactide-co-glycolide-co-ε-caprolactone); and wherein the weight ratio of the first poly(D,L-lactide-co-glycolide-co-ε-caprolactone) to the second poly(D,L-lactide-co-glycolide-co-ε-caprolactone) is from about 90:10 to about 60:40. Terpolymer compositions having adhesive properties are described in U.S. Pat. No. 8,920,921, the content of which is herein incorporated by reference in its entirety.

In some embodiments, the matrix can include a blend of (a) a poly(D,L-lactide-co-glycolide-co-ε-caprolactone) having a molecular weight of from 75,000 to 250,000 Daltons and a polydispersity index (PDI) of less than 2.0, and (b) a poly(D,L-lactide-co-glycolide-co-mPEG) having a molecular weight ($M_w$) of less than 25,000 Daltons and a polydispersity index (PDI) of less than 2.0; the poly(D,L-lactide-co-glycolide-co-mPEG) having a molecular weight ($M_w$) that is less than the poly(D,L-lactide-co-glycolide-co-ε-caprolactone); and wherein the weight ratio of the poly(D,L-lactide-co-glycolide-co-ε-caprolactone) to the poly(D,L-lactide-co-glycolide-co-mPEG) is from about 95:5 to about 75:25.

Other suitable biodegradable polymers include, but are not limited to, poly(trimethylene carbonate) (PTMC), polydioxanone (PDO), poly(4-hydroxy butyrate) (PHB), and poly(butylene succinate) (PBS), poly(trimethylene carbonate) (PTMC), polydioxanone (PDO), poly(4-hydroxy butyrate) (PHB), and poly(butylene succinate) (PBS).

In another embodiment, the polymeric material or polymer is biostable. Examples of biostable polymers include, but are not limited to polyurethanes, silicone rubbers, styrene-isobutylene-styrene block copolymers, ether-ester block copolymers (e.g., 1500-40D from RTP Co.) and vinyl materials, including but not limited to poly(ethylene-co-vinyl acetate) (PEVA).

In various embodiments, the controlled release matrix includes an elastomeric polymeric material that includes a copolymer with an elastomeric (or "soft") component and a non-elastomeric (or "hard") component. In another embodiment, the elastomeric polymeric material includes a polymeric blend having an elastomeric component and a non-elastomeric component.

In various embodiments, the compliant polymer or polymeric material is thermoplastic. As used herein, the term "thermoplastic" refers to a polymer or polymeric material that can be softened by heat, hardened by cooling and then softened by heat over and over again. In general, thermoplastic materials are not cross-linked. However, in another embodiment, the compliant polymer or polymeric material may be cross-linked.

Method of Making

The bioactive agent can be incorporated into the controlled release matrix any of various techniques known to the skilled artisan. In various embodiments, the bioactive agent is dispersed throughout the controlled release matrix. Techniques for preparing the controlled release matrix include, but are not limited to, melt extrusion processes, injection molding, or spray casting.

In a melt extrusion process, a mixture that includes the polymeric material and bioactive agent is combined in an extruder, heated to a temperature at which the polymeric material melts and then discharged through an orifice of the desired cross-sectional shape. The extruded material is collected under controlled conditions (e.g., speed, temperature and humidity) to obtain a product with the desired dimensions. In various embodiments, the mass flow rate of the extrudate and the collection speed of the final extruded form can be controlled to achieve the desired physical dimensions. For example, if the final extruded form is a film, then the collection speed of the film can be increased relative to the mass flow rate of the extrudate to decrease the film thickness, and conversely to increase the film thickness. The extrudate is discharged through an orifice in the molten state, allowing elongation of the extrudate to its final dimension. The extrudate is subsequently cooled by exposure to ambient conditions, a chilled liquid or gas bath, or exposure to a temperature controlled surface such as a cooled roller in order to solidify the exturdate. In various embodiments, the melt extrusion process is used to form a film. In an alternate embodiment, the melt extrusion process is used to form pellets or beads that can be subsequently molded into the desired film or collar configuration. Some of the advantages of melt extrusion processes include: the absence of organic solvents and high throughput, continuous manufacturing. In general, the processing temperature is sufficient to melt the polymeric material without adversely affecting the biological activity of the bioactive agent. In general, the processing temperature is at least about 80° C., or about 100° C. and less than about 180° C., less than 160° C., or between about 110° C. and about 150° C., although the specific temperature is dependent on the melting and degradation temperatures of the polymeric materials and bioactive agent. Furthermore, melt-processing provides the ability for continuous operation, the ability to control operating parameters, and the ability to scale up manufacturing.

In an alternate embodiment, an injection molding process is used. In an injection molding process, a mixture that includes the polymeric material and bioactive agent is fed into a vessel where it heated to a temperature sufficient to melt the polymeric material and then forced into a mold cavity where it cools and hardens to the configuration of the mold cavity. The conditions (e.g., temperature and pressure) will depend upon the material being molded. In various embodiments, the injection molding process is used to form a film or a collar.

In yet another embodiment, a solvent casting technique can be used. In a solvent casting process, the polymeric material and bioactive agent are combined with a suitable solvent to form a polymeric solution which is then cast on a substrate. The solvent is then removed to form a film, for example, by evaporation. In various embodiments, the solvent is removed under a vacuum (e.g., between about 15 inHg and about 28 inHg, depending upon the volatility of the solvent). In another embodiment, the solvent is removed at an elevated temperature (e.g., between about 30° C. and about 80° C.). In an alternate embodiment, the polymeric solution is applied to the substrate by a spray coating process. In a spray coating process, the polymeric solution is fed to the spray nozzle, for example and ultrasonic spray nozzle, at a controlled rate by a positive displacement pump. The spray nozzle and substrate are moved in relative motion to each other at controlled speed to achieve the desired coating thickness. The spray nozzle is mounted on a three-axis motion control system (x-y-z) which is capable of controlling the speed and position of the spray head relative to the substrate. In addition, if the substrate is a rolled film, it is traversed below the spray head by a roll to roll unwinding and winding apparatus. The coating width is controlled by moving the spray nozzle in a specified path across the width of the substrate. In addition, the height (z) of the spray nozzle above the substrate can be increased to achieve a wider coating width.

The solvent may be one in which one or more components of the polymeric material form a true solution. The bioactive agent may either be soluble in the solvent or form a dispersion throughout the solvent. Suitable solvents include, but are not limited to, alcohols (e.g., methanol, butanol, propanol and isopropanol), alkanes (e.g., halogenated or unhalogenated alkanes such as hexane, cyclohexane, methylene chloride and chloroform), amides (e.g., dimethylformamide), ethers (e.g., tetrahydrofuran (THF), dioxolane, and dioxane), ketones (e.g., methyl ethyl ketone, acetone), aromatic compounds (e.g., toluene and xylene), nitriles (e.g., acetonitrile) and esters (e.g., ethyl acetate). THF and chloroform have been found to be suitable solvents due to their excellent solvency for a variety of polymers and bioactive agents.

Excipients

In various embodiments, the polymeric matrix includes one or more plasticizers, tackifiers, or other excipients, for example, to introduce an adhesive to one side of the film, or to increase the overall release rate of active ingredients from the film (e.g., by decreasing the glass transition of the polymer).

Medical Device

The controlled release matrix barrier structure described herein can be provided as individually packaged and pre-sterilized units in a kit such that a medical practitioner is able to apply the controlled release matrix barrier structure to an implantable medical device, for example, while in the operating room. In various embodiments, the entire surface of the medical device is covered with the controlled release matrix barrier structure. In another embodiment, the surface of the medical device is only partially covered with the controlled release matrix barrier structure. For example, a single strip or narrow collar of the controlled release matrix barrier structure can be applied to a portion of the medical device, wherein a majority of the surface of the medical device remains uncovered. In an alternate embodiment, a majority of the surface of the medical device can be covered with the controlled release matrix barrier structure, but select areas can be left unwrapped, for example, for fixation hardware attachment. The dosage of bioactive agent can be modified by altering the amount of controlled release matrix barrier structure that is applied to the medical device, for example, a higher dosage of bioactive agent can be achieved by increasing the amount (or length) of controlled release matrix that is applied to the medical device. Similarly, a lower dosage of bioactive agent can be achieved by decreasing the amount (or length) of controlled release matrix that is applied to the medical device. In various embodiments, the packaging material for the controlled release matrix barrier structure provides an indication of the amount of drug per unit length. The concentration of bioactive agent in the controlled release matrix can vary, but is generally between about 2% by weight and about 50% by weight of the controlled release matrix. The dosage per unit length can vary, but is generally between 21 micrograms per millimeter and 525 micrograms per millimeter for a 7 mm wide and 150 micron thick film.

The controlled release matrix provides a means to deliver bioactive agents from a variety of biomaterial surfaces. Suitable biomaterials include those formed of synthetic polymers, including oligomers, homopolymers, and copolymers resulting from either addition or condensation polymerizations. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls, such as those polymerized from ethylene, propylene, styrene, vinyl chloride, vinyl acetate, vinyl pyrrolidone, and vinylidene difluoride. Examples of condensation polymers include, but are not limited to, nylons such as polycaprolactam, poly(lauryl lactam), poly(hexamethylene adipamide), and poly(hexamethylene dodecanediamide), and also polyurethanes, polycarbonates, polyamides, polysulfones, poly(ethylene terephthalate), poly(lactic acid), poly(glycolic acid), poly(lactic acid-co-glycolic acid), polydimethylsiloxanes, polyetheretherketone, poly(butylene terephthalate), poly(butylene terephthalate-co-polyethylene glycol terephthalate), esters with phosphorus containing linkages, non-peptide polyamino acid polymers, polyiminocarbonates, amino acid-derived polycarbonates and polyarylates, and copolymers of polyethylene oxides with amino acids or peptide sequences.

Certain natural materials are also suitable biomaterials, including human tissue such as bone, cartilage, skin and teeth; and other organic materials such as wood, cellulose, compressed carbon, and rubber. Other suitable biomaterials include metals and ceramics. The metals include, but are not limited to, titanium, stainless steel, and cobalt chromium. A second class of metals include the noble metals such as gold, silver, copper, and platinum. Alloys of metals, such as nitinol (e.g. MP35), may be suitable for biomaterials as well. The ceramics include, but are not limited to, silicon nitride, silicon carbide, zirconia, and alumina, as well as glass, silica, and sapphire. Yet other suitable biomaterials include combinations of ceramics and metals, as well as biomaterials that are fibrous or porous in nature.

In various embodiments, the biomaterial substrate is a resorbable material (i.e., a material that can be degraded or broken down in vivo and assimilated into the body of the patient).

The controlled release matrix barrier structure described herein is suitable for use in connection with a variety of implantable medical devices. Examples of suitable medical devices include, but are not limited to, spinal fixation devices such as those used to achieve vertebral fixation, including rods, plates, screws, and combinations thereof. Other medical devices include, but are not limited to, surgical devices (e.g., staples, bone pins, suture anchors, clamps, screws, plates, clips, etc.); cardiovascular devices (e.g., pacemakers and defibrillation systems, including, but not limited to, electro-stimulation leads for cardiac rhythm management such as pacer or defibrillator leads; and structural cardiac applications, including, but not limited to tissue and mechanical valves, and patent foramen ovale closure systems), biosensors; orthopedic devices (e.g., joint implants, fracture repairs); and dental implants.

In various embodiments, controlled release matrix barrier structures herein are used in conjunction with medical devices having one or more subcutaneous elements. Subcutaneous elements are those that when placed for use pass through the skin. In some cases, such subcutaneous elements are placed for a duration longer than merely transitorily. Medical devices with subcutaneous elements can include, but are not limited to, ventricular assist devices (VADs), central venous catheters, implanted drug delivery ports (such as chemotherapy ports), implantable monitors, neuromodulation devices with wired external controllers or monitors.

Figure 6:
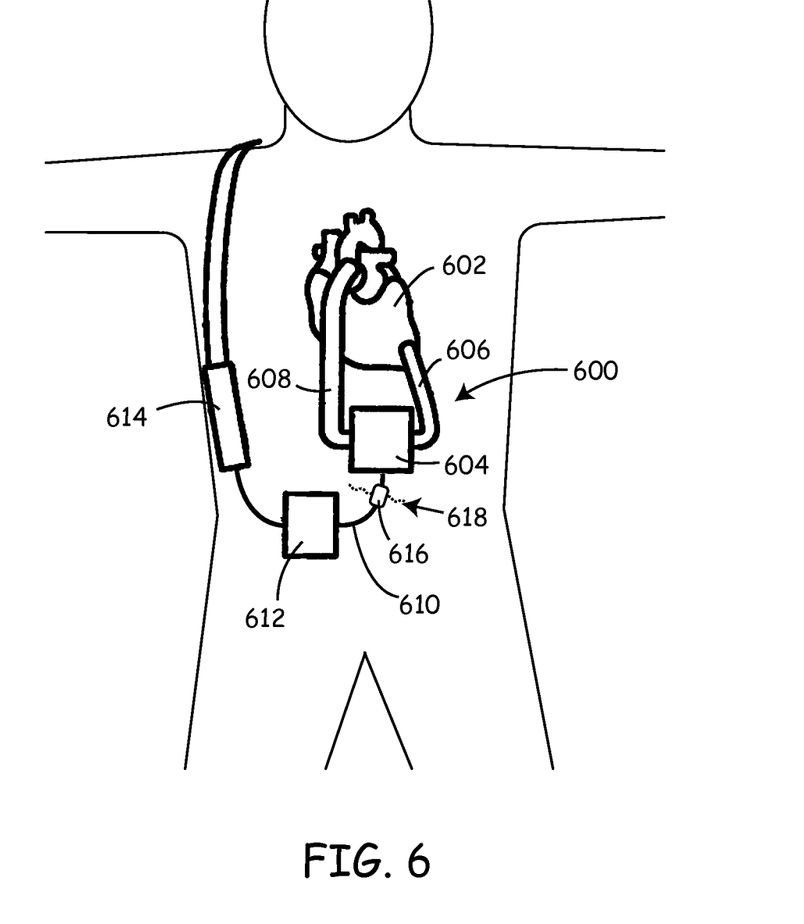
FIG. 6 is a schematic illustration of a medical device with a subcutaneous element and a controlled release matrix barrier structure device applied thereto.

Referring now to FIG. 6, a schematic illustration of a medical device 600 is shown with a subcutaneous element and a controlled release matrix barrier structure applied thereto. The medical device 600, in this example, is a ventricular assist device (VAD) operatively connected to the heart 602 of a patient. Aspects of VADs are described in U.S. Pat. Nos. 4,995,857 and 7,993,260, the content of which is herein incorporated by reference. The medical device 600 includes blood flow conduits (606, 608) a pump 604, power and/or data transmission cable 610 (or "driveline" that crosses the skin 618 and therefore can be regarded as a subcutaneous element) a control unit 612, and a power unit 614. A controlled release matrix barrier structure 616 is operatively connected to the power and/or data transmission cable 610. In various embodiments, the controlled release matrix barrier structure 616 can be in full circumferential contact with the subcutaneous element such that there are no places where microorganisms can pass in gaps between the inner diameter of the controlled release matrix barrier structure 616 and the outer diameter of the subcutaneous element. While not intending to be bound by theory, embodiments wherein the controlled release matrix barrier structure is compliant can facilitate full circumferential contact and the formation of an effective barrier.

Figure 7:
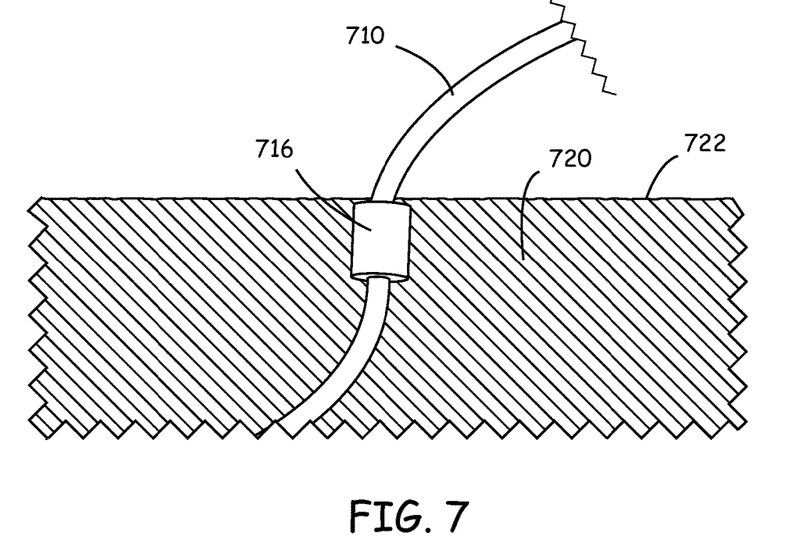
FIG. 7 is a schematic illustration of a controlled release matrix barrier structure applied to a subcutaneous element of a medical device.

Referring now to FIG. 7, a schematic illustration of a controlled release matrix barrier structure 716 applied to a subcutaneous element 710 of a medical device is shown in accordance with various embodiments herein. In this embodiment, the controlled release matrix barrier structure 716 is positioned underneath the skin 722 and within the tissue 720 of the patient. However, it will be appreciated that other configurations are contemplated herein. By way of example, the controlled release matrix barrier structure 716 can be only partially within the tissue 720 of the patient. Alternatively, the controlled release matrix barrier structure 716 can be completely outside of the tissue 720 of the patient.

Figure 8:
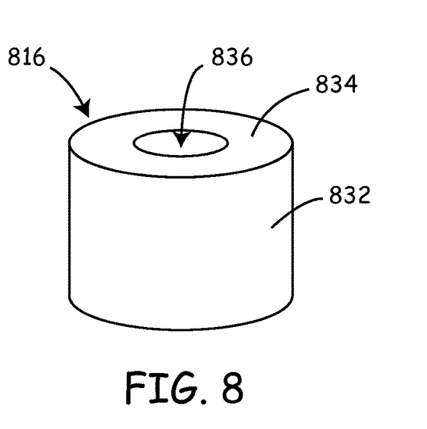
FIG. 8 is a schematic illustration of a controlled release matrix barrier structure configured for use with a medical device with a subcutaneous element in accordance with various embodiments herein.

FIG. 8 is a schematic illustration of a controlled release matrix barrier structure 816 configured for use with a medical device with a subcutaneous element in accordance with various embodiments herein. The controlled release matrix barrier structure 816 includes a body structure 832 and an outer surface 834. In some embodiments, the outer surface 834 is positioned beneath the skin of the patient. In other embodiments, the outer surface 834, or a portion thereof is positioned outside the skin of the patient. The body structure 832 defines a central channel 836 (or aperture or lumen), through which the subcutaneous element of the medical device can pass. In some embodiments, the barrier structure can include an inner surface adjacent the central channel and an adhesive, such as a terpolymer exhibiting adhesive properties, disposed on the inner surface. In some embodiments, the controlled release matrix barrier structure 816 can be pre-formed as a tube (or as a collar or sheath) and the subcutaneous element can be threaded there through. The tube can be circumferentially continuous or can have a separation line along the lengthwise axis of the tube to accommodate opening of the tube. In other embodiments, the controlled release matrix barrier structure 816 can be formed by wrapping one or more layers (such as film layers) of the controlled release matrix barrier structure 816 materials around the subcutaneous element.

Figure 9:
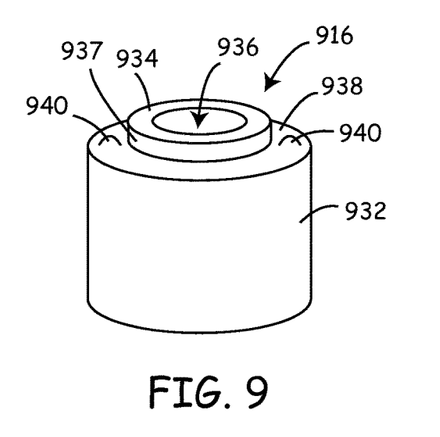
FIG. 9 is a schematic illustration of a controlled release matrix barrier structure configured for use with a medical device with a subcutaneous element in accordance with various embodiments herein.

Various other features can be included with embodiments of the controlled release matrices herein. By way of example, in some embodiments, the controlled release matrix barrier structure can include a flange, or peripheral shoulder, around the top portion adjacent the outer surface. Referring now to FIG. 9, a schematic illustration of a controlled release matrix barrier structure 916 configured for use with a medical device with a subcutaneous element in accordance with various embodiments herein is shown. The controlled release matrix barrier structure 916 can include a body structure 932 defining a central channel 936 (or aperture or lumen), through which the subcutaneous element of the medical device can pass. In some embodiments, the controlled release matrix barrier structure 916 can also include suture loops 940 to aid in using sutures to secure the controlled release matrix barrier structure 916 to the skin.

The controlled release matrix barrier structure 916 can include a flange 938 or shoulder and a central projection 937 upon which the outer surface 934 is disposed. In some embodiments, the skin of the patient can fit against the flange or shoulder and the central projection can pass through the skin to the outside.

Bioactive Agent

The controlled release matrix barrier structure described herein can be used in connection with a variety of bioactive agents. As used herein, the term "bioactive agent" refers to a wide range of biologically active materials that causes a biological effect when administered in vivo to an animal. The term "bioactive agent" includes hydrophobic and hydrophilic molecules, including, but not limited to, macromolecules (i.e., molecules with a molecular weight of at least about 1000 Da) such as peptides, proteins, carbohydrates, nucleic acids, lipids, polysaccharides or combinations thereof; or synthetic or natural organic or inorganic molecules. The term "animal" includes, but is not limited to, birds and mammals, including humans. A comprehensive listing of bioactive agents can be found in The Merck Index, Thirteenth Edition, Merck & Co. (2001), the entire contents of which is incorporated by reference herein.

The concentration of bioactive agent within the controlled release matrix can vary depending upon a variety of factors, including the agent and its intended use, i.e. short or long duration. In various embodiments, the bioactive agent concentration in the controlled release matrix is between about 2% to about 50% by weight, or about 10% to about 40% by weight, or about 15% to about 30% by weight.

In various embodiments, the bioactive agent is hydrophobic. As used herein, the term "hydrophobic" refers to a bioactive agent that has a solubility in water of no more than 200 micrograms per milliliter. In another embodiment, the bioactive agent is hydrophilic. As used herein, the term "hydrophilic" refers to a bioactive agent that has a solubility in water of more than 200 micrograms per milliliter.

Classes of bioactive agents that can be incorporated into the controlled release matrix include, but are not limited to, antibiotics, antiseptics, antiviral agents, enzyme inhibitors, anti-pyretics, including anti-inflammatory agents, immunomodulators, including immunosuppressants and corticosteroids, analgesics, local anesthetics, and cell response modifiers. A more complete listing of classes of medicaments may be found in the Pharmazeutische Wirkstoffe, ed. A. Von Kleemann and J. Engel, Georg Thieme Verlag, Stuttgart/New York, 1987, incorporated herein by reference.

Antibiotics are recognized as substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, geldanamycin, geldanamycin analogues and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceflizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

In some embodiments, the bioactive agent is selected from antibiotics and antiseptics.

Anti-viral agents are substances capable of destroying or suppressing the replication of viruses. Examples of anti-viral agents include methyl-P-adamantane methylamine, hydroxy-ethoxymethylguanine, adamantanamine, 5-iodo-2'-deoxyuridine, trifluorothymidine, interferon, and adenine arabinoside.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine, 1-hydroxymaleate, iodotubercidin, p-bromotetramisole, 10-(.alpha.-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N-monomethyl-L-arginine acetate, carbidopa, 3-hydroxybenzylhydrazine HCl, hydralazine HCl, clorgyline HCl, deprenyl HCl, L(−), deprenyl.HCl, D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacin, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, R(+), p-aminoglutethimide tartrate, S(−), 3-iodotyrosine, alpha-methyltyrosine, L(−), alpha-methyltyrosine, D L(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (acetylsalicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances which inhibit pain signals in a localized region. Examples of such anesthetics include procaine, lidocaine, tetracaine and dibucaine.

Imaging agents are agents capable of imaging a desired site, e.g., tumor, in vivo. Examples of imaging agents include substances having a label which is detectable in vivo, e.g., antibodies attached to fluorescent labels. The term antibody includes whole antibodies or fragments thereof.

Cell response modifiers are chemotactic factors such as platelet-derived growth factor (pDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor (alpha), fibroblast growth factor, platelet-derived endothelial cell growth factor, estradiols, insulin-like growth factor, nerve growth factor, bone growth/cartilage-inducing factor (alpha and beta), and matrix metallo proteinase inhibitors. Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin. Vascular endothelial growth factor (VEGF) is a chemical signal produced by cells that stimulates the growth of new blood vessels. VEGF inhibitors can be used to treat diseases such as cancers, which require an adequate blood supply to grow and metastasize. DNA that encodes for the production of any of these proteins, antisense molecules, androgenic receptor blockers and statin agents can also be a bioactive agent.

EXAMPLES

Example 1

A controlled release matrix containing a bioactive agent can be prepared as follows. A mixture of 15% bioactive agent (such as dexamethasone acetate) is combined with a polymeric matrix such as poly(lactic-co-glycolic acid) polymer (PLGA) and melt extruded using a twin screw extruder (available from American LEISTRITZ Extruder Corp. USA, Somerville, N.J. 08876). The bioactive agent is fed in a continuous manner to the twin screw extruder from a loss-in-weight feeder (available from K-Tron International, Inc., Pitman, N.J. 08071). The polymeric matrix is fed in a similar manner. The ratio of the bioactive agent to the polymeric matrix is controlled by the relative mass flow rate of bioactive agent from the first feeder to that of the polymeric matrix from the second feeder. The feeders and extruder are purged with dry air or nitrogen gas to maintain low humidity. The polymeric matrix is melted within the extruder operating at a temperature of 120° C. The bioactive agent is not melted but is mixed within the molten and flowing polymeric matrix. The extruder forces or pumps the mixed bioactive agent and polymeric matrix through a rectangular shaped orifice or die to shape the material into an extrudate with width of between about 5 mm and about 10 mm and a thickness between about 50 µm and about 250 µm. After cooling, the extrudate is cut into strips with a desired length and packaged. The individual strips are placed and sealed inside of a sterilization pouch such as foil-foil pouch (available from 445 Sixth Street, NW, Grand Rapids, Mich. 49504 USA).

As used herein, the term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

The phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive.

We claim:

1. A biocompatible polymeric controlled release matrix barrier structure comprising:
    a body structure formed of a compliant material comprising one or more compliant biocompatible polymers and one or more bioactive agents; and
    the body structure defining a central aperture through which a subcutaneous element of an implantable medical device passes;
    wherein the body structure further comprises an inner surface adjacent the central aperture, wherein the inner surface is circumferentially continuous; and at least a first poly(D,L-lactide-co-glycolide-co-ε-caprolactone) terpolymer disposed on the inner surface;
    wherein the controlled release matrix barrier structure further comprises a central projection that is disposed about the central aperture at a top portion of the body structure and a flange disposed around the central projection, the flange having an outer surface with one or more suture loops disposed thereon; and
    wherein the central projection extends in a direction away from the body structure.

2. The biocompatible polymeric controlled release matrix barrier structure of claim 1, wherein the biocompatible polymer is biostable or biodegradable.

3. The biocompatible polymeric controlled release matrix barrier structure of claim 1, wherein the controlled release matrix barrier structure comprises a polymer selected from the group consisting of: polycaprolactone (PCL), poly(lactic acid), poly(lactic-co-glycolic acid), and poly(ethylene-co-vinyl acetate).

4. The biocompatible polymeric controlled release matrix barrier structure of claim 3, wherein the polymers are not cross-linked.

5. The biocompatible polymeric controlled release matrix barrier structure of claim 1, wherein the bioactive agent is selected from the group consisting of antibiotics and antiseptics.

6. A biocompatible polymeric controlled release matrix barrier structure comprising:
    a body structure comprising an elastomeric collar comprising one or more elastomeric biocompatible polymers and one or more bioactive agents;
    the body structure defining a central aperture through which a subcutaneous element of an implantable medical device passes;
    wherein the body structure further comprises an inner surface adjacent the central aperture, wherein the inner surface is circumferentially continuous; and at least a first poly(D,L-lactide-co-glycolide-co-ε-caprolactone) terpolymer exhibiting adhesive properties disposed on the inner surface;
    wherein the controlled release matrix barrier structure further comprises a central projection that is disposed about the central aperture at a top portion of the body structure and a flange disposed around the central projection, the flange having an outer surface with one or more suture loops disposed thereon; and
    wherein the central projection extends in a direction away from e body structure.

7. The biocompatible polymeric controlled release matrix barrier structure of claim 6, wherein the biocompatible polymer is biostable or biodegradable.

8. The biocompatible polymeric controlled release matrix barrier structure of claim 6, wherein the controlled release matrix barrier structure comprises a polymer selected from the group consisting of: polycaprolactone (PCL), poly(lactic acid), poly(lactic-co-glycolic acid), and poly(ethylene-co-vinyl acetate).

9. The biocompatible polymeric controlled release matrix barrier structure of claim 6, wherein the polymers are not cross-linked.

10. The biocompatible polymeric controlled release matrix barrier structure of claim 6, wherein the bioactive agent is selected from the group consisting of antibiotics and antiseptics.

11. The biocompatible polymeric controlled release matrix barrier structure of claim 1, wherein the poly(D,L-lactide-co-glycolide-co-ε-caprolactone) has a molecular weight from 75,000 to 250,000 Daltons and a polydispersity index (PDI) of less than 2.0.

12. The biocompatible polymeric controlled release matrix barrier structure of claim 6, wherein the poly(D,L-lactide-co-glycolide-co-ε-caprolactone) of has a molecular weight from 75,000 to 250,000 Daltons and a polydispersity index (PDI) of less than 2.0.

13. The biocompatible polymeric controlled release matrix barrier structure of claim 1, the body structure further comprising a second poly(D,L-lactide-co-glycolide-co-ε-caprolactone).

14. The biocompatible polymeric controlled release matrix barrier structure of claim 13, the second poly(Dl-lactide-co-glycolide-co-ε-caprolactone) having a molecular weight from 130,000 Daltons or less and a polydispersity index (PDI) of less than 2.0, and wherein the molecular weight of the second poly(D,L-lactide-co-glycolide-co-ε-caprolactone) is less than the molecular weight of the first poly(D,L-lactide-co-glycolide-co-ε-caprolactone).

* * * * *